(12) United States Patent
Farazi et al.

(10) Patent No.: US 7,627,374 B1
(45) Date of Patent: Dec. 1, 2009

(54) SYSTEM AND METHOD FOR EVALUATING AND OPTIMIZING THE CONTRIBUTION OF PARTICULAR HEART CHAMBERS TO THE OVERALL EFFICACY OF CARDIAC PACING THERAPY

(75) Inventors: Taraneh Ghaffari Farazi, San Jose, CA (US); Euljoon Park, Valencia, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 454 days.

(21) Appl. No.: 11/421,936

(22) Filed: Jun. 2, 2006

(51) Int. Cl.
*A61N 1/362* (2006.01)
(52) U.S. Cl. .......................................................... 607/9
(58) Field of Classification Search .................. 607/7, 607/9, 11, 17, 28
See application file for complete search history.

(56) References Cited

U.S. PATENT DOCUMENTS

| | | | |
|---|---|---|---|
| 5,188,106 A | 2/1993 | Nappholz et al. | |
| 5,328,460 A | 7/1994 | Lord et al. | |
| 5,487,752 A | 1/1996 | Salo et al. | |
| 5,540,727 A * | 7/1996 | Tockman et al. | 607/18 |
| 5,615,684 A | 4/1997 | Hagel et al. | |
| 5,626,623 A | 5/1997 | Kieval et al. | |
| 5,779,645 A | 7/1998 | Olson et al. | |
| 5,800,467 A | 9/1998 | Park et al. | |
| 5,891,176 A * | 4/1999 | Bornzin | 607/18 |
| 5,893,882 A * | 4/1999 | Peterson et al. | 607/14 |
| 6,370,427 B1 * | 4/2002 | Alt et al. | 607/4 |
| 6,516,219 B1 | 2/2003 | Street | |
| 6,575,912 B1 | 6/2003 | Turcott | |
| 6,622,045 B2 | 9/2003 | Snell et al. | |
| 6,997,879 B1 | 2/2006 | Turcott | |
| 2004/0030356 A1 | 2/2004 | Osypka | |

FOREIGN PATENT DOCUMENTS

| | | |
|---|---|---|
| WO | 03092804 | 11/2003 |
| WO | WO 2005123178 | 12/2005 |

* cited by examiner

*Primary Examiner*—Carl H Layno
*Assistant Examiner*—Brian T Gedeon
(74) *Attorney, Agent, or Firm*—Steven M. Mitchell; Theresa A. Takeuchi

(57) ABSTRACT

Techniques are provided for evaluating and optimizing the contribution of particular heart chambers to pacing efficacy. Briefly, a pacemaker temporarily alters the mode with which pacing therapy is delivered so as to selectively alter the heart chambers that are paced. The pacemaker detects any transient changes in pacing efficacy following the alteration in pacing mode. The pacemaker then assesses the contribution of particular heart chambers to pacing efficacy based on the alteration in the pacing mode and on any transient changes in the pacing efficacy. Additionally, techniques are provided herein for automatically adjusting pacing parameters to optimize the contribution of particular chambers to pacing efficacy.

20 Claims, 10 Drawing Sheets

US 7,627,374 B1

SYSTEM AND METHOD FOR EVALUATING AND OPTIMIZING THE CONTRIBUTION OF PARTICULAR HEART CHAMBERS TO THE OVERALL EFFICACY OF CARDIAC PACING THERAPY

FIELD OF THE INVENTION

The invention generally relates to implantable cardiac stimulation devices for use in pacing the heart and in particular to techniques for optimizing pacing parameters to improve pacing efficacy.

BACKGROUND OF THE INVENTION

A pacemaker is an implantable cardiac stimulation device for implant within a patient that analyzes an intracardiac electrogram (IEGM) to detect various arrhythmias, such as an abnormally slow heart rate (bradycardia) or an abnormally fast heart rate (tachycardia), and then to selectively deliver electrical pacing pulses to the heart in an effort to remedy the arrhythmias. An implantable cardioverter-defibrillator (ICD) additionally or alternatively detects atrial fibrillation (AF) or ventricular fibrillation (VF) and delivers electrical shocks to terminate fibrillation. For many patients, particularly those with congestive heart failure (CHF), it is desirable to identify a set of control parameters for controlling the operation of the pacemaker or ICD that will optimize cardiac performance (also referred to as hemodynamic performance). Cardiac performance is a measure of the overall effectiveness of the cardiac system of a patient and is typically represented in terms of stroke volume or cardiac output. Stroke volume is the amount of blood ejected from the left ventricle during systole in the forward direction. Cardiac output is the volume of blood pumped by the left ventricle per minute (i.e. stroke volume multiplied by the current heart rate of the patient).

One particularly useful control parameter for optimizing cardiac performance is the atrioventricular (A-V) pacing delay, which for dual-chamber devices specifies the time delay between a paced or sensed atrial event and a paced ventricular event. Another useful control parameter is the inter-ventricular pacing delay (V-V), which for biventricular pacing devices specifies the time delay between a paced or sensed right ventricular (RV) event and a paced left ventricular (LV) event. However, a wide variety of other parameters also affect overall cardiac performance. Numerous techniques have been developed for optimizing these and other parameters so as to improve cardiac performance. See, for example, U.S. patent application Ser. No. 11/366,930, of Muller et al., entitled "System and Method for Determining Atrioventricular Pacing Delay Based on Atrial Repolarization," filed Mar. 1, 2006; U.S. patent application Ser. No. 10/928,586, of Bruhns et al., entitled "System and Method for Determining Optimal Atrioventricular Delay based on Intrinsic Conduction Delays", filed Aug. 27, 2004; U.S. patent application Ser. No. 11/231,081, of Turcott, entitled "System and Method for Rapid Optimization of Control Parameters of an Implantable Cardiac Stimulation Device", filed Sep. 19, 2005; and U.S. patent application Ser. No. 11/199,619, of Gil et al., entitled "System and Method for Determining Preferred Atrioventricular Pacing Delay Values based on Intracardiac Electrogram Signals", filed Aug. 8, 2005.

Although an improvement in cardiac performance is often the goal, pacing therapy may alternatively be delivered to achieve other goals or to obtain other benefits. For example, for a patient suffering from high blood pressure, pacing therapy may be delivered so as to decrease blood pressure. If a patient is at risk of certain arrhythmias, pacing therapy may be tailored so as to decrease the risk of the arrhythmia. In one specific example, wherein a patient is subject to atrial tachyarrhythmias, dynamic atrial overdrive (DAO) pacing may be delivered so as to reduce the risk of such arrhythmias. In still other examples, pacing therapy is delivered so as to reduce the risk of VF. As can be appreciated, a wide variety of pacing parameters may be selectively adjusted so as to achieve a wide variety of goals. Hence, stated generally, pacing parameters are preferably optimized to enhance overall "pacing efficacy," where the efficacy of pacing is evaluated with respect to the particular goal of the pacing regime. Numerous techniques have been previously developed for use by implantable medical devices to automatically adjust pacing parameters so as to improve overall pacing efficacy within the context of specific pacing regimes, such as the techniques of the patent applications listed above.

Heretofore, however, it does not appear that many techniques have been developed specifically for evaluating and optimizing the contribution of particular chambers to pacing efficacy. That is, predecessor techniques generally seek to determine pacing parameters that will improve overall pacing efficacy without regard to the specific contribution provided by particular heart chambers, such as just the right atrial (RA) contribution or just the LV contribution. By evaluating the contribution of particular chambers to pacing efficacy, the device can provide diagnostic information from which the physician can gain considerable insight into the health of those chambers. Moreover, an evaluation of the contribution of particular chambers to pacing efficacy can be exploited by the device itself to enhance or optimize the contribution of those chambers. In many cases, by optimizing the contribution of particular chambers to pacing efficacy, the device can thereby improve overall pacing efficacy so as to, for example, improve overall cardiac performance. Accordingly, it would be desirable to provide techniques for evaluating and optimizing the contribution to pacing efficacy provided by particular heart chambers. It is to this end that the invention is primarily directed.

SUMMARY OF THE INVENTION

In accordance with the invention, techniques are provided for evaluating and optimizing the contribution of particular chambers to pacing efficacy. In one embodiment, the device temporarily alters the pacing mode with which pacing therapy is delivered, wherein the mode specifies which chambers of the heart are paced. The device detects any transient changes in pacing efficacy following the alteration in pacing mode. The device then determines the contribution of particular heart chambers to the pacing efficacy based on the alteration in pacing mode and on any transient changes in pacing efficacy. For example, by temporarily switching from biventricular pacing to RV-only pacing, the device can evaluate the contribution of the LV to pacing efficacy. In this regard, if there is little or no reduction in pacing efficacy despite disabling LV pacing, then the LV contributes little to pacing efficacy. In contrast, a significant reduction in pacing efficacy following the switch to RV-only pacing is indicative of a significant contribution of the LV to pacing efficacy. As another example, by temporarily switching from dual-chamber pacing (i.e. atrial and ventricular pacing) to ventricle-only pacing, the device can evaluate the contribution of the atria to pacing efficacy. Depending upon the particular goal of a pacing regime, the efficacy of pacing therapy can be evaluated based on signals representative of, e.g., blood oxygen saturation, blood pressure, contractility, stroke volume, or cardiac output sensed via appropriate implanted sensors or evaluated based on morphological features of the IEGM. Diagnostic information indicative of the contribution of the particular chambers to pacing efficacy is preferably stored within the device for subsequent physician review. The degree of contribution can also be compared against suitable thresholds indicative of a minimum acceptable degree of chamber contribution, with appropriate warning signals generated if the degree of contribution falls below the threshold to thereby alert the patient and/or physician.

In a preferred embodiment, the implantable device additionally adjusts selected pacing parameters so as to optimize the contribution of particular chambers. For example, during dual-chamber pacing, the A-V delay can be adjusted so as to optimize the contribution of the atria to pacing efficacy. As another example, during biventricular pacing, the V-V delay can be adjusted so as to optimize the LV contribution to pacing efficacy. In many cases, optimizing the contribution of particular chambers serves to improve overall pacing efficacy so as to, for example, improve overall cardiac performance. Preferably, a given pacing parameter is incrementally adjusted throughout a predetermined range of acceptable values. The implantable device evaluates the degree of contribution of selected heart chambers at each value of the parameter. The implantable device then chooses the value of the parameter that achieved the greatest degree of contribution for use in further pacing so as to optimize the contribution of the selected heart chambers. In one particular example, V-V delay values are incrementally adjusted throughout a range of V-V values. At each particular V-V value, the device temporarily switches from biventricular pacing to RV-only pacing and then evaluates the contribution of the LV to pacing efficacy at that particular V-V value. The V-V value that yields the greatest contribution of the LV to pacing efficacy is then selected for use in further biventricular pacing. As another example, A-V delay values are incrementally adjusted throughout a predetermined range of A-V values. At each particular A-V value, the device temporarily switches from dual-chamber pacing to ventricular-only pacing and then evaluates the contribution of the atria to pacing efficacy at that particular A-V value. The A-V value that yields the greatest contribution of the atria to pacing efficacy is then selected for use in further dual-chamber pacing.

Thus, techniques are provided for evaluating and optimizing the contribution of particular chambers to pacing efficacy. Since only a temporary alteration in pacing mode is needed to assess the contribution of particular chambers, the technique can be frequently performed by the device to assess chamber-specific contributions and to adjust and optimize the pacing parameters accordingly. Although the invention is advantageously implemented with the implantable device itself, principles of the invention are also applicable for use by external devices, such as external programmers used in conjunction with implantable devices.

BRIEF DESCRIPTION OF THE DRAWINGS

The above and further features, advantages and benefits of the invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Medical System

Figure 1:
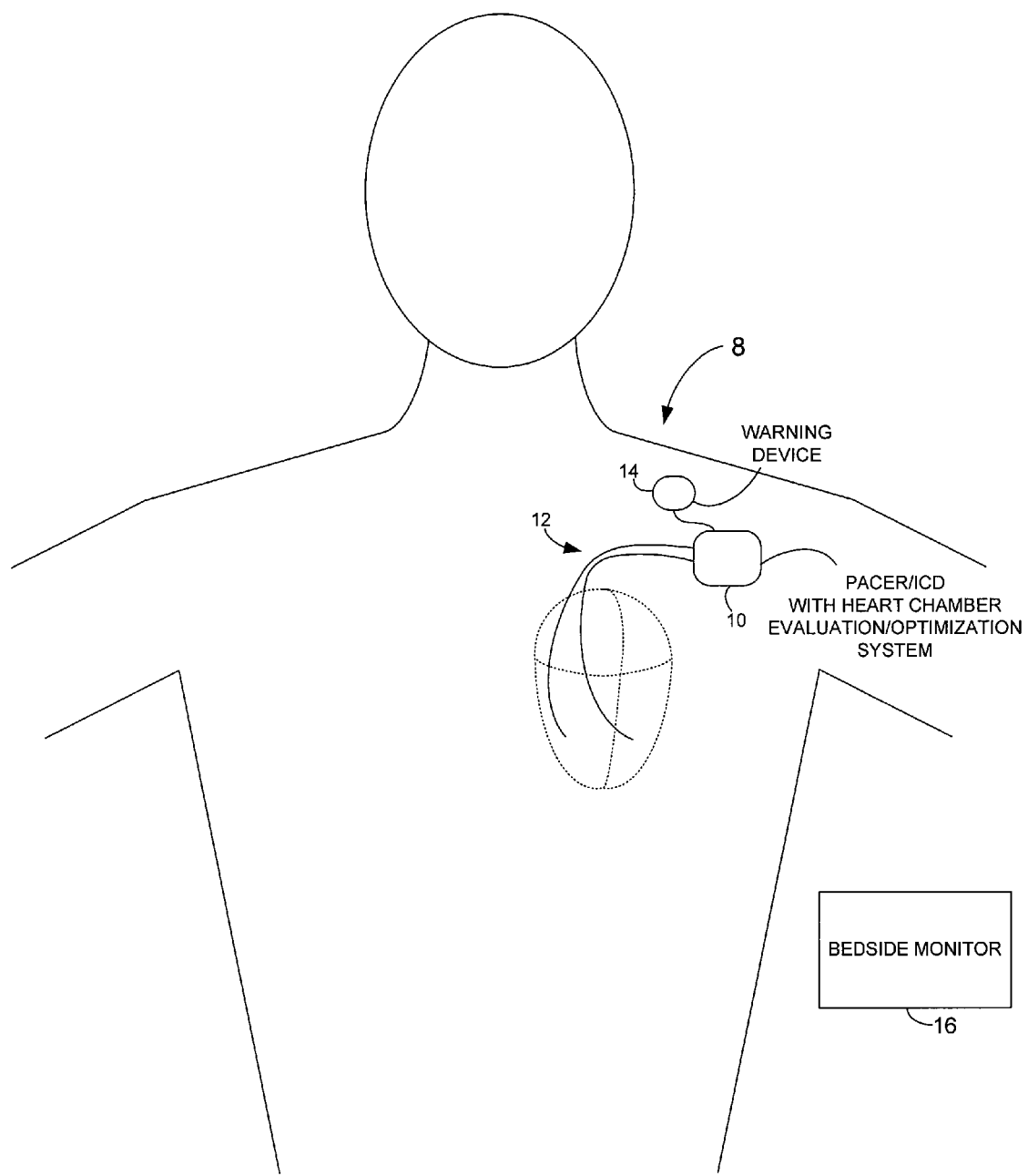
FIG. 1 illustrates pertinent components of an implantable medical system having a pacemaker or ICD equipped to evaluate and optimize the contribution of particular heart chambers to pacing efficacy.
Figure 9:
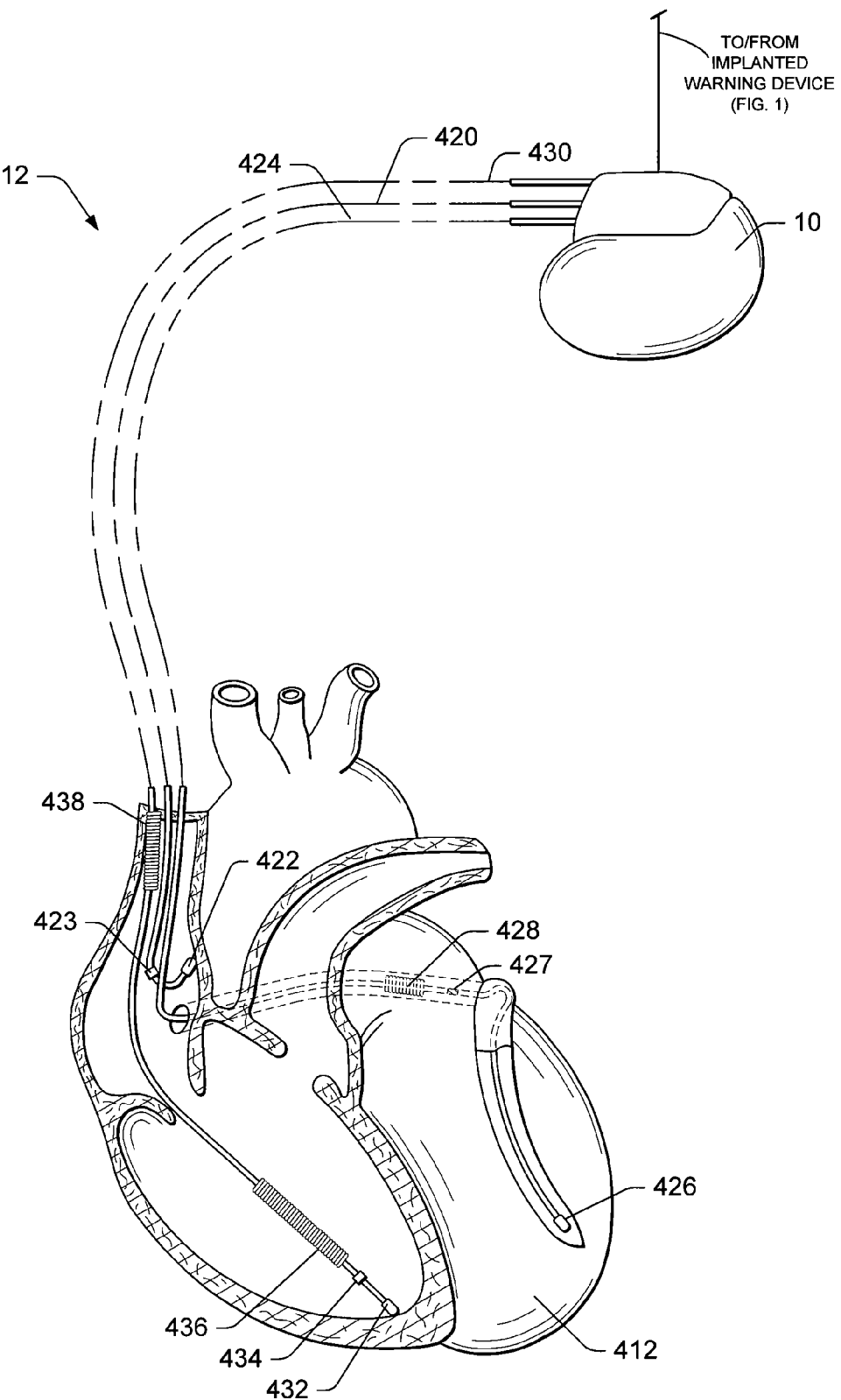
FIG. 9 is a simplified, partly cutaway view, illustrating the pacer/ICD of FIG. 1 along with a set of exemplary leads implanted in the heart of the patient.

FIG. 1 illustrates an implantable medical system 8 having a pacer/ICD 10 equipped to evaluate the contribution of particular heart chambers to pacing efficacy, such as only the atrial contribution or only the contribution of the RV. Depending upon the goal of a particular pacing regime, the contribution to pacing efficacy may be evaluated based on an analysis of IEGM signals sensed via a set of pacing leads 12 or based on physiological signals received from various sensors (not separately shown in FIG. 1.) Only a pair of leads is shown. A more complete set of pacing/sensing leads is illustrated in FIG. 9 and is described below. Once the contribution of the particular chamber or chambers has been evaluated, pacing parameters are automatically adjusted by pacer/ICD 10 so as to optimize the contribution of the particular chambers. In many cases, optimizing the contribution of particular chambers serves to enhance overall pacing efficacy to, e.g., improve overall cardiac performance. If the contribution of particular chambers is found to be deficient, suitable warning signals may be generated using an internal warning device 14, if one is provided. Warning device 14 may be a vibrating device or a "tickle" voltage device that, in either case, provides perceptible stimulation to the patient to alert the patient. Tickle warning device are discussed in U.S. Pat. No. 5,328, 460 to Lord, et al., entitled "Implantable Medication Infusion Pump Including Self-Contained Acoustic Fault Detection Apparatus." Warning signals may additionally or alternatively be transmitted to a bedside monitor 16, which generates audible or visual warnings. The bedside monitor may be networked with other external systems so as to automatically forward the warnings to a physician or other medical professional. A system incorporating bedside monitoring units connected to a centralized external programmer system is described in U.S. Pat. No. 6,622,045 to Snell et al., "System and Method for Remote Programming of Implantable Cardiac Stimulation Devices." In this manner, if the contribution of a particular chamber, such as the LV, is found to be deficient due to cardiomyopathy or other ailments, the physician can be notified to take corrective action.

Thus, FIG. 1 provides an overview of an implantable medical system for evaluating and optimizing the contribution of particular heart chambers to pacing efficacy. It should be appreciated that systems provided in accordance with invention need not include all of the components shown in FIG. 1. In many cases, for example, the implantable system will include only the pacer/ICD and its leads with no implantable warning device. The bedside monitor is optional. No attempt is made herein to describe all possible combinations of components that may be provided in accordance with the general principles of the invention. Note also that, although an internal signal transmission line interconnecting the pacer/ICD and the implantable warning device is shown, wireless signal transmission may alternatively be employed. In addition, the particular size, shapes and implant locations of the various components are merely illustrative and do not necessarily correspond to the actual sizes, shapes and locations.

Overview of Heart Chamber Contribution Evaluation

FIG. 1 provides an overview of the evaluation technique performed by the pacer/ICD of FIG. 1 or other suitable device. Initially, at step 100, the pacer/ICD temporarily alters the current pacing mode. The pacing mode specifies, among other attributes, which chambers of the heart are paced. Many such pacing modes are specified by standard three letter codes such as: AAI; VVI; DDD; DDI; VDD; and VOO. Briefly, the first letter of the code designates which chamber is paced (A for atrium, V for ventricle, D for both, and O for neither). The second letter designates which chamber is sensed. The third letter designates what action is taken in response to a sense (I for inhibiting delivery of a pacing pulse, T for triggering a pacing pulse, D for both triggering and inhibiting, depending upon the chamber, and O for no action). A fourth letter R is sometimes appended to the code if a rate-adaptive pacing mode is used.

Thus, by way of example, DDD indicates a pacing mode wherein the pacer/ICD senses and paces in both the atria and the ventricles and is also capable of both triggering and inhibiting functions based upon events sensed in the atria and the ventricles. VDD indicates a mode wherein the pacer/ICD senses in both the atria and ventricles but only paces in the ventricles. A sensed event on the atrial channel triggers ventricular outputs after a programmable delay. VVI indicates that the pacer/ICD paces and senses only in the ventricles and only inhibits the functions based upon events sensed in the ventricles. DDI is identical to DDD except that the pacer/ICD only inhibits functions based upon sensed events, rather than triggering functions. As such, the DDI mode is a non-tracking mode precluding triggering of ventricular outputs in response to sensed atrial events. VOO identifies fixed-rate ventricular pacing, which ignores any potentially sensed cardiac signals. This mode is quite different from the aforementioned "demand" modes, which only pace when the pacemaker determines that the heart is "demanding" pacing. Other pacing modes are possible that are not necessarily represented by three letter abbreviations of this type. For example, if the pacer/ICD is equipped for biventricular pacing, then the pacing mode may further specify whether pacing or sensing is performed in the LV, the RV or both. Likewise, if the pacer/ICD is equipped for biatrial pacing, then the pacing mode may further specify whether pacing or sensing is performed in the RA, the left atrium (LA) or both. As can be appreciated, numerous pacing modes are possible and no attempt is made herein to list all such modes.

The period of time during which the pacing mode is altered may vary depending upon the particular pacing modes and the pacing efficacy to be evaluated. Typically, however, the pacing mode is temporarily altered for a period of between two and sixty seconds. At step 102, the pacer/ICD detects transient changes in the efficacy of pacing therapy following the alteration in pacing mode at step 100. Pacing efficacy is defined with respect to the goal of the pacing regime. For example, if pacing is performed so as to increase cardiac performance, then an increase in cardiac performance indicates an increase in pacing efficacy. The increase in cardiac performance may be quantified using, e.g., stroke volume, cardiac output, etc. In contrast, if pacing is performed so as to affect a change in a particular morphological feature of the IEGM, perhaps to reduce the risk of certain arrhythmias, then a change in the amplitude of that morphological feature indicates an increase in pacing efficacy. Hence, depending upon the circumstances, any of a wide variety of parameters may be sensed to provide an indication of pacing efficacy. Other examples include: blood oxygen saturation, blood pressure, contractility, or the shape of a heart output pulse waveform.

Techniques for evaluating morphological features of the IEGM are described in: U.S. Pat. No. 5,779,645 to Olson, et al. entitled "System and Method for Waveform Morphology Comparison" and U.S. Pat. No. 6,516,219 to Street, entitled "Arrhythmia Forecasting Based on Morphology Changes in Intracardiac Electrograms." Techniques for detecting blood oxygen saturation using an implantable medical device are described in: U.S. patent application Ser. No. 11/378,604, of Kroll et al., filed Mar. 16, 2006, entitled, "System and Method for Detecting Arterial Blood Pressure based on Aortic Electrical Resistance using an Implantable Medical Device" (A05e1123). Techniques for detecting blood pressure are described in: U.S. Pat. No. 5,615,684 to Hagel, et al., entitled "Medical Device for Detecting Hemodynamic Conditions of a Heart" and U.S. Pat. No. 6,575,912 to Turcott, entitled "Assessing Heart Failure Status Using Morphology of a Signal Representative of Arterial Pulse Pressure." Techniques for detecting contractility are described in: U.S. Pat. No. 5,800, 467 to Park et al., entitled "Cardio-Synchronous Impedance Measurement System for an Implantable Stimulation Device." Techniques for detecting stroke volume and/or cardiac output are described in U.S. patent application Ser. No. 11/267,665, filed Nov. 4, 2005, of Kil et al., entitled "System and Method for Measuring Cardiac Output via Thermal Dilution using an Implantable Medical Device with Thermistor Implanted in Right Ventricle." The heart pulse output waveform may be sensed using an implantable photoplethysmograph (PPG), which is an optical detector that indicates the volume of blood in or passing through an area of tissue. By placing the photoplethysmograph around an artery, the pulse waveform can be detected and measured. Implantable PPG devices are discussed, e.g., in U.S. Pat. No. 6,997,879 to Turcott, entitled "Methods and Devices for Reduction of Motion-induced Noise in Optical Vascular Plethysmography."

In many cases, multiple parameters may be combined to provide a combined measure or "metric" of pacing efficacy. Techniques for combining different parameters into a single metric value for evaluation are set forth in U.S. Pat. No. 7,207,947 to Koh et al., entitled "System and Method for Detecting Circadian States Using an Implantable Medical Device", issued Apr. 24, 2007.

Figure 3:
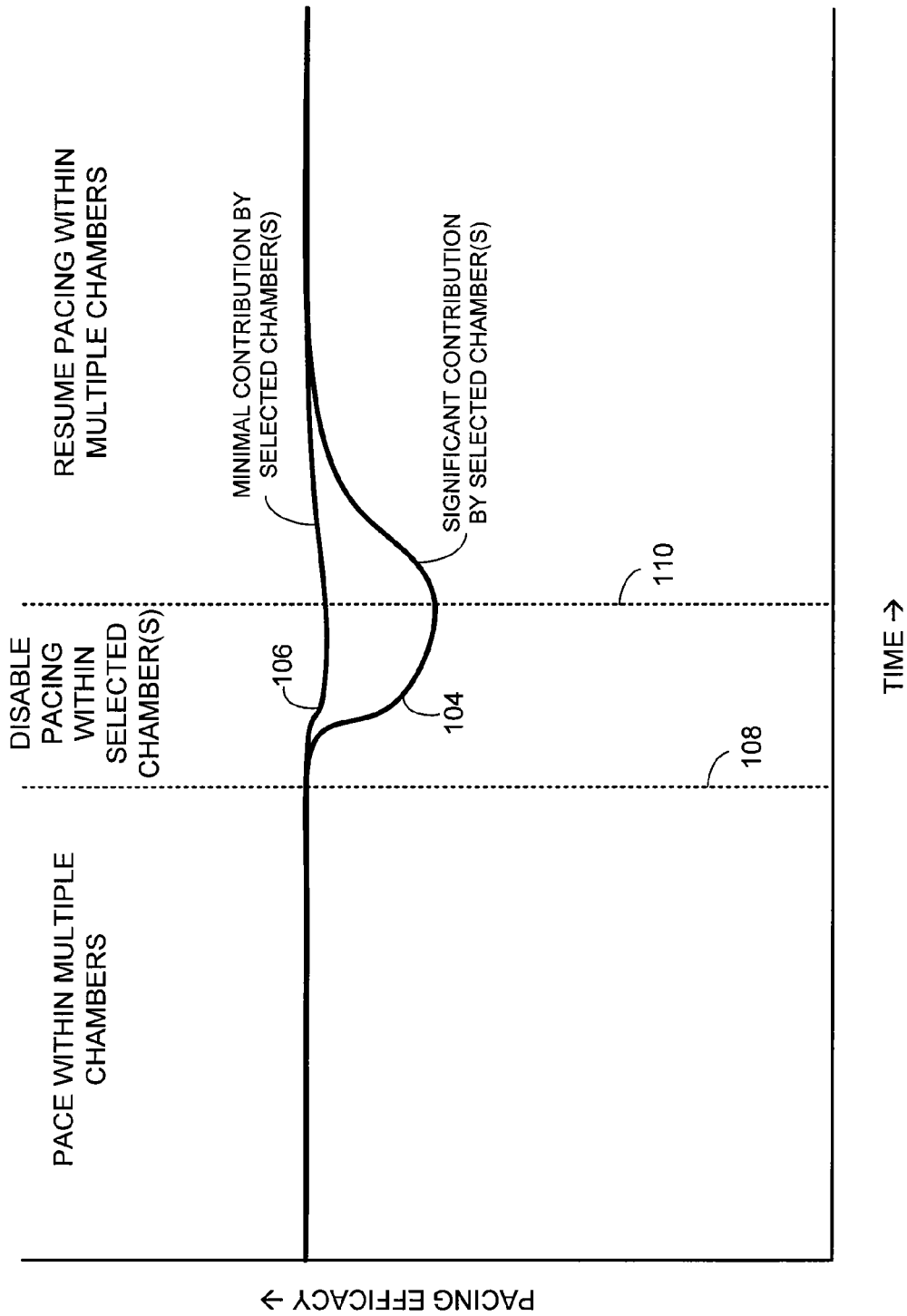
FIG. 3 is a graph illustrating an exemplary pacing efficacy curve and particularly illustrating a transient reduction in pacing efficacy following a temporary change in pacing mode performed in accordance with the technique of FIG. 2.

FIG. 3 illustrates exemplary pacing efficacy curves 104 and 106 subject to transient variations following a temporary change in pacing mode. The pacing efficacy curves of FIG. 3 are intended to represent any of a variety of exemplary pacing efficacy parameters such as stroke volume, blood pressure, contractility, etc. or a combination thereof. Initially, pacing is provided within two or more chambers. At time 108, the pacing mode is altered to disable pacing in at least one chamber. At time 110, pacing reverts the original mode. Pacing may be disabled in at least one chamber by, for example, switching from DDI to VVI pacing or by switching from biventricular pacing to RV-only pacing. As can be seen, there is a transient reduction in pacing efficacy caused by the temporary alteration in pacing mode. In the specific example of curve 104, the reduction is significant, indicating that the chamber or chambers where pacing had been disabled were providing a significant contribution to pacing efficacy. In the specific example of curve 106, the reduction is not significant, indicating that the chamber or chambers where pacing had been disabled were providing only a minimal contribution to pacing efficacy. Preferably, diagnostic information representative of the transient alteration in pacing efficacy is stored for automatic analysis and physician review. Note that the curves illustrated in the graphs of FIG. 3, and in the various other graphs described herein, should not be construed as depicting actual clinically-obtained data. The curves set forth hypothetical data provided to clearly illustrate features of the invention. Hence, actual transient variations in pacing efficacy may differ.

Returning to FIG. 2, at step 112, the pacer/ICD determines the contribution of particular heart chambers to the overall efficacy of pacing therapy based on the alteration in pacing mode and on any transient changes in the observed pacing efficacy. That is, the pacer/ICD analyzes curves such as those presented in FIG. 3 to evaluate the contribution of the chambers that had pacing temporarily disabled. In one example, the pacer/ICD quantifies the reduction in pacing efficacy as a contribution index value. For example, if the pacing mode is altered from DDI to VVI so as to temporarily disable pacing in the atria, the numerical decrease in pacing efficacy may be represented as an atrial contribution index. As another example, if the pacing mode is altered from biventricular to RV-only so as to temporarily disable pacing in the LV, the numerical decrease in pacing efficacy may be represented as an LV contribution index. Preferably, the index values and/or other appropriate diagnostic information are recorded for subsequent physician review. As already noted, warning signals may be generated if the contribution of a particular chamber is deemed to be deficient.

At step 114, the pacer/ICD automatically adjusts pacing parameters so as to modify a particular heart chamber's contribution to pacing efficacy. For example, if the initial alteration in pacing mode was performed to evaluate the atrial contribution to pacing efficacy, the pacing parameters may be adjusted so as to optimize the atrial contribution. Techniques for implementing step 114 will be described in greater detail below with reference to FIGS. 4-8. Typically, the pacing parameters are adjusted so as to maximize a selected chamber's contribution to pacing efficacy. However, in some cases, it may be appropriate to selectively reduce a given chamber's contribution. In other cases, if particular chambers are found not to contribute significantly to pacing efficacy, pacing within those chambers may simply be disabled to prevent waste of power within the device. Typically, these decisions are made by a physician based on the measured contribution index and other factors. However, in some cases, the device itself may be programmed to automatically deactivate pacing within particular chambers. This may be achieved merely be changing the pacing mode to a mode where the particular chambers are not paced.

Figure 2:
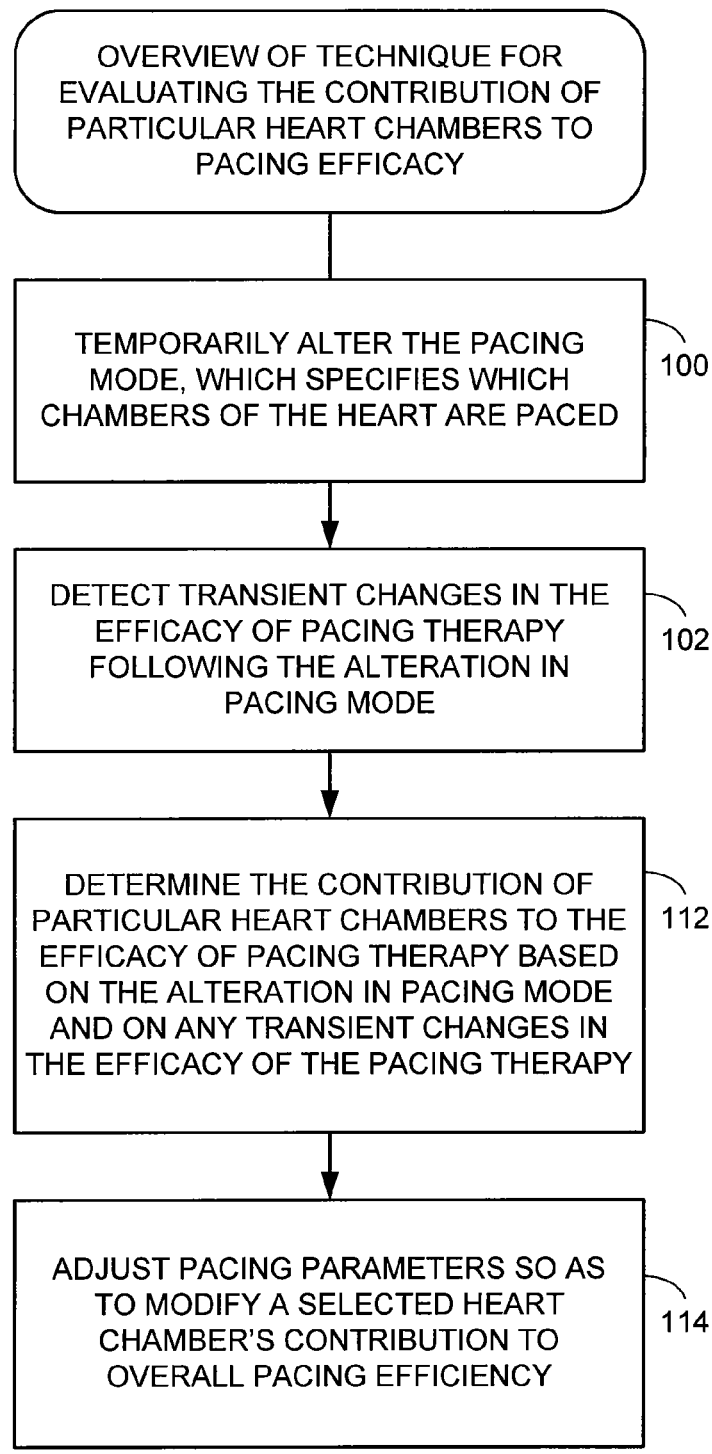
FIG. 2 is a flow chart providing an overview of an exemplary evaluation technique for use by the implantable system of FIG. 1 wherein transient changes in pacing efficacy are detected following temporary changes in pacing mode.

Thus, FIGS. 2 and 3 provide an overview of the heart chamber contribution evaluation techniques of the invention. Turning now to FIGS. 4-8, techniques for optimizing a given chamber's contribution to pacing efficacy will now be described.

Heart Chamber Contribution Optimization Techniques

Figure 4:
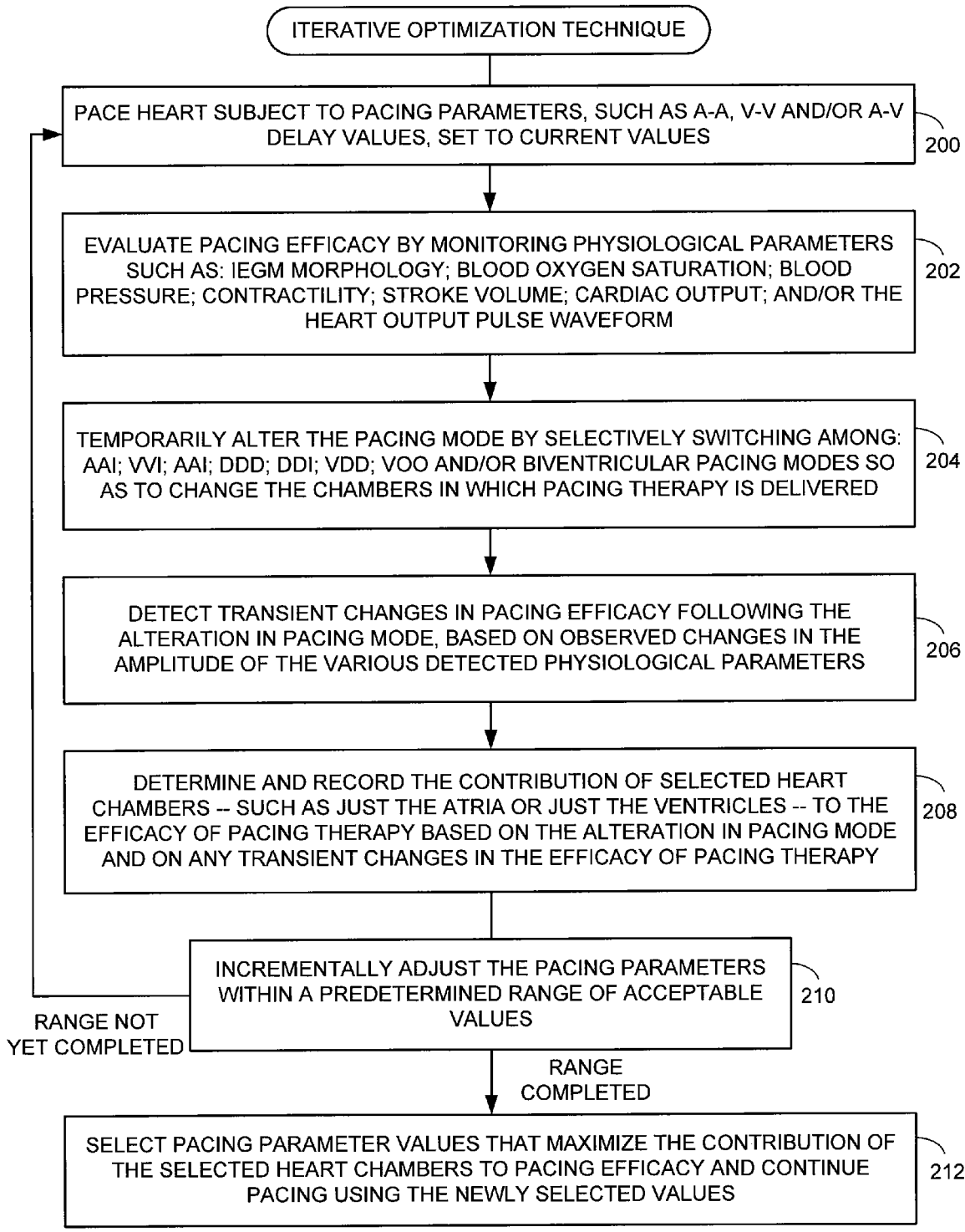
FIG. 4 is a flow chart illustrating an iterative optimization technique performed in accordance with the general evaluation technique of FIG. 2, wherein pacing parameters are iteratively adjusted to optimize chamber-specific contributions to pacing efficacy.

FIG. 4 illustrates an iterative technique for optimizing pacing parameters to maximize the contributions of particular heart chambers to pacing efficacy. Briefly, in this iterative technique, the evaluation steps of FIG. 1 are repeated while iteratively adjusting pacing parameters through a range of values to determine the particular values yielding the greatest pacing efficacy. Beginning at step 200, the pacer/ICD paces the heart subject to one or more pacing parameters, such as A-V, V-V and/or A-A delay values, set to current values. The current values may be, e.g., default values or values set as a result of a previous optimization session. At step 202, the pacer/ICD evaluates overall pacing efficacy by monitoring physiological parameters such as one or more: blood oxygen saturation; blood pressure; contractility; stroke volume; cardiac output; heart output pulse waveform and/or morphological features of the IEGM. At step 204, the pacer/ICD temporarily alters the pacing mode by switching, e.g., among: AAI; VVI; DDD; DDI; VDD; and/or VOO modes or between biventricular and monoventricular pacing modes, so as to selectively change the chambers in which pacing therapy is delivered. At step 206, the pacer/ICD detects transient changes in pacing efficacy following the alteration in pacing mode based on observed changes in the amplitude of the appropriate physiological parameter. At step 208, the pacer/ICD determines and records the contribution of selected heart chambers—such as just the atria or just the ventricles—to the overall efficacy of pacing therapy based on the alteration in pacing mode and on any transient changes in the efficacy of pacing therapy. Steps 200-208 generally correspond to steps 100-102 and 112 of FIG. 1.

At step 210, the pacer/ICD incrementally adjusts selected pacing parameters within a predetermined range of acceptable values. Examples will be described below wherein A-V and V-V delay parameters are incrementally adjusted. However, a wide variety of other pacing parameters may alternatively be adjusted. The predetermined range of values depends upon the parameter being adjusted and is typically specified by the programming of the device. In many cases, parameters can only be set to certain discrete values within the range of values. Incremental adjustment then simply involves setting the parameter to another of the predetermined discrete values. Processing then returns to step 200 so that steps 200-208 can be repeated to evaluate the contribution of the selected heart chambers using the new pacing parameters. Typically, only one parameter is adjusted at a time. However, in some implementations, it may be appropriate to adjust two or more parameters simultaneously. In any case, once steps 200-208 have been repeated with the new parameter values, the parameters are incrementally adjusted yet again, and the process repeats until iterative adjustment throughout the entire predetermined range of values is complete. Finally, at step 212, the pacer/ICD then selects the particular pacing parameter values that maximize the contribution of the selected heart chambers to pacing efficacy and then continues pacing using the newly selected values. In many cases, optimizing the contribution of an individual chamber serves to improve overall pacing efficacy to, for example, improve overall cardiac performance. Preferably, the procedure of FIG. 4 is repeated periodically, such as once per week, to update the pacing parameters to account for any changes in the health of the patient, any changes in prescribed medications, etc. Ideally, the optimization procedure is performed at about the same time during the day and under the same conditions so that variations in patient activity and posture do not unduly influence the optimization procedure. In one example, the procedure is performed only at night while the patient is asleep.

Figure 5:
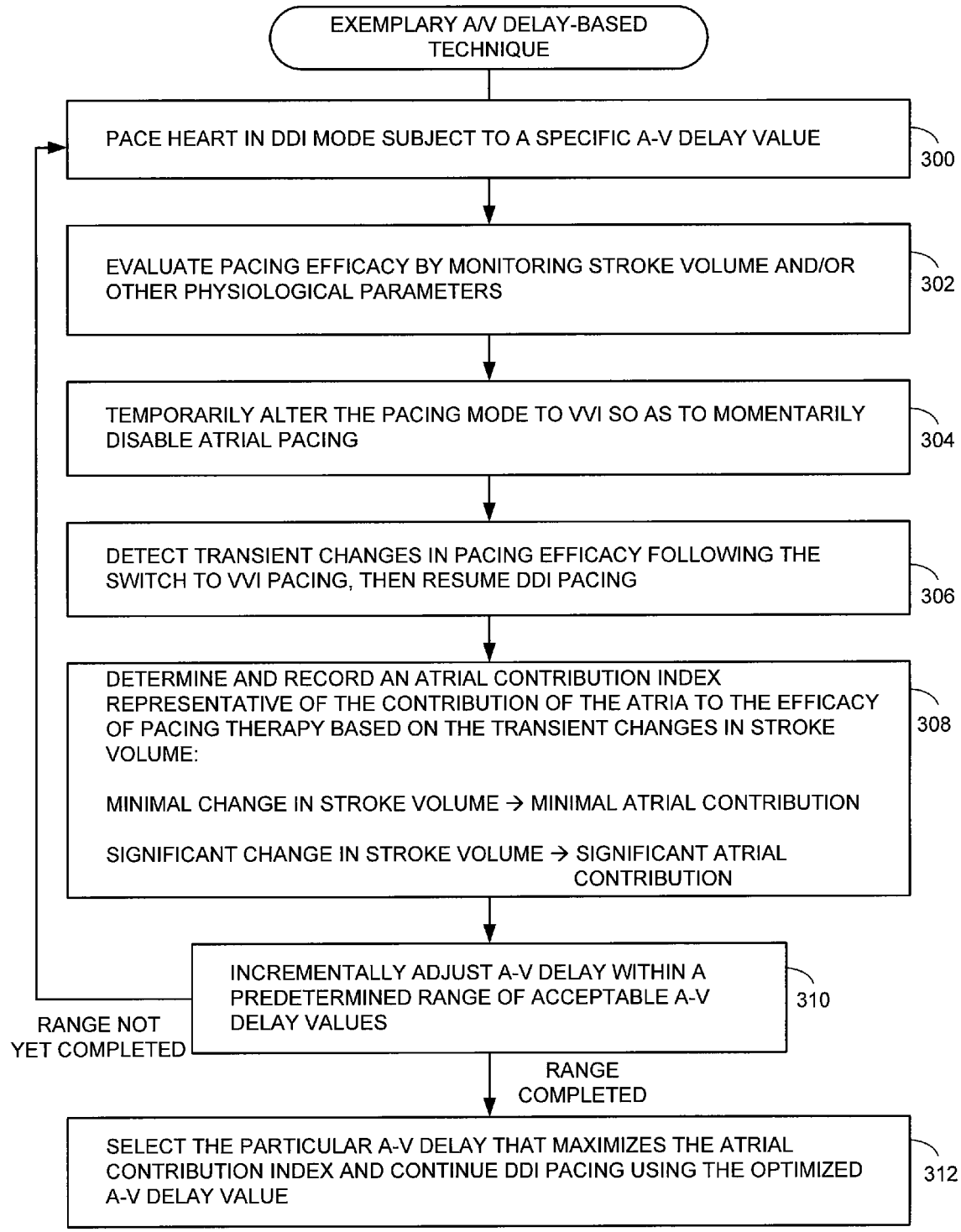
FIG. 5 is a flow chart illustrating a first exemplary implementation of the iterative technique of FIG. 4, wherein an A-V delay is iteratively adjusted to optimize the atrial contribution to stroke volume during dual-chamber pacing.
Figure 6:
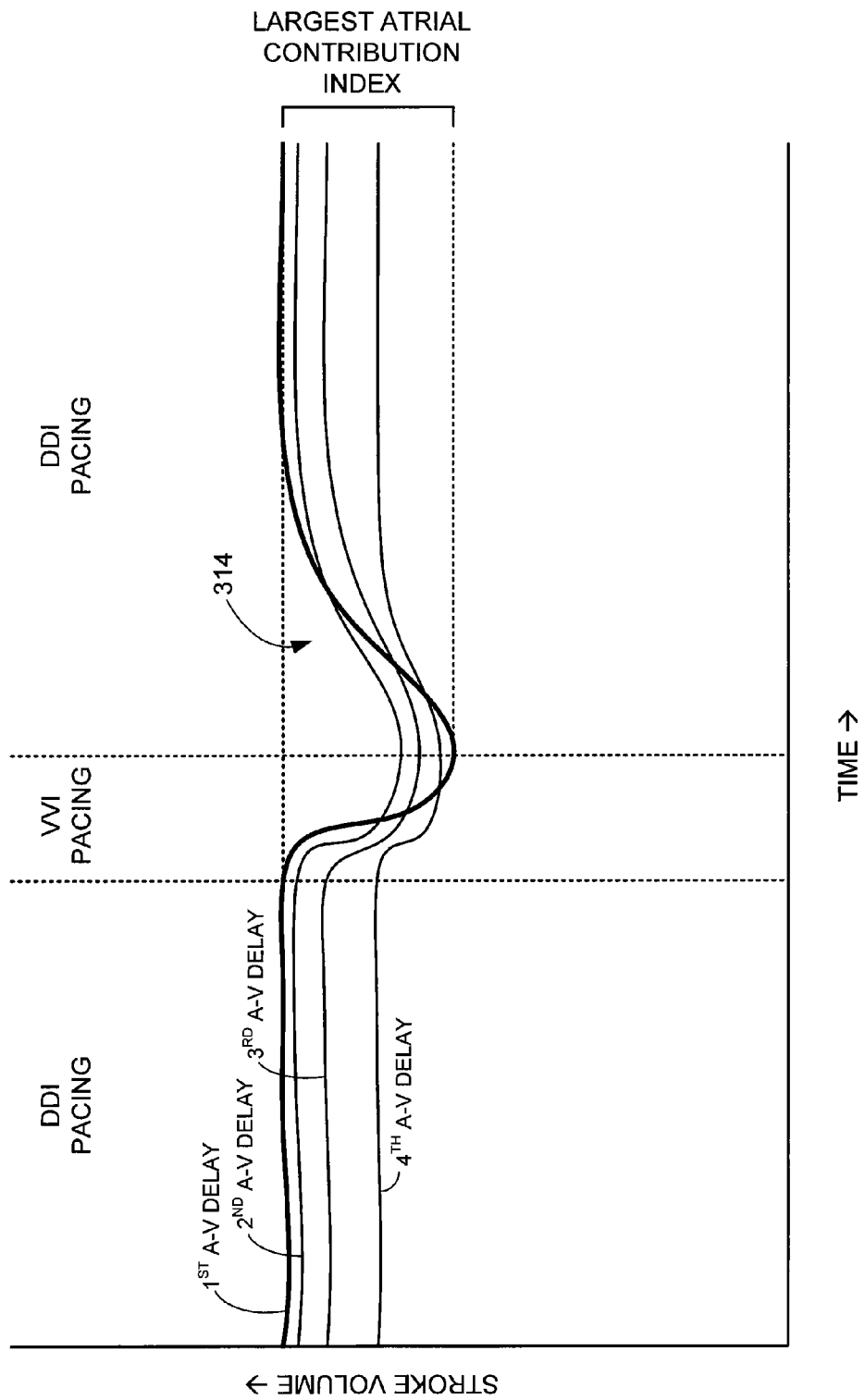
FIG. 6 is a graph illustrating a set of exemplary stroke volume curves and particularly illustrating transient reductions in stroke volume following temporary changes from DDI to VVI pacing performed in accordance with the iterative technique of FIG. 5.

Two specific examples will now be described with reference to FIGS. 5-8. In the example of FIGS. 5-6, an A-V delay value is adjusted so as to optimize the atrial contribution to cardiac performance, as measured by stroke volume. At step 300, the pacer/ICD paces the heart in DDI mode subject to a specific A-V delay value, which may be, e.g., a default value or a value set via a previous optimization session. At step 302, the pacer/ICD evaluates pacing efficacy by monitoring stroke volume and/or other relevant physiological parameters. At step 304, the pacer/ICD temporarily alters the pacing mode to VVI so as to momentarily disable atrial pacing. At step 306, the pacer/ICD detects transient changes in pacing efficacy following the switch to Vvl pacing, then resumes DDI pacing. At step 308, the pacer/ICD determines and records an "atrial contribution index" representative of the contribution of the atria to the efficacy of pacing therapy based on the transient changes in stroke volume. In this regard, a minimal change in stroke volume is indicative of minimal contribution of the atria to pacing efficacy. A significant change in stroke volume is indicative of a more significant contribution of the atria to pacing efficacy. At step 310, the pacer/ICD incrementally adjusts the A-V delay within a predetermined range of acceptable values. Typically, this is achieved by merely resetting the A-V delay value to a different one of a set of permissible A-V values already programmed into the device. Steps 300-308 are repeated at the new A-V delay value to assess the atrial contribution to pacing efficacy at that new A-V delay value, until all or most of the permissible values for the A-V delay have been tested. Finally, at step 312, the pacer/ICD selects the particular A-V delay yielding the largest atrial contribution index and then continues DDI pacing using the selected A-V delay value. In this manner, the contribution of the atria to enhanced stroke volume is maximized.

FIG. 6 illustrates a set of four exemplary stroke volume curves 314 recorded during four iterations of the steps of FIG. 5. The curves are shown superimposed over one another so as to emphasize the differences therebetween. In actuality, the curves are obtained sequentially over a period of time by iteratively adjusting the A-V delay, then temporarily switching the pacing mode from DDI to VVI, as just described. A first curve illustrates the transient reduction in stroke volume observed while pacing is performed with the A-V delay set to a first specific A-V delay value (during DDI pacing); a second curve illustrates the transient reduction in stroke volume observed while pacing is performed with the A-V delay set to a second specific A-V delay value (during DDI pacing); and so on, up to a 4th A-V delay value. In each case, the reduction in stroke volume from DDI to VVI is quantified as the atrial contribution index, which represents the difference in stroke volume between the volume observed just prior to the switch to VVI and the minimum stroke volume occurring as a result of the switch the VVI. Hence, each curve has a different atrial contribution index associate therewith.

In the particular example of FIG. 6, the largest atrial contribution index is observed while the first A-V delay value is used. This particular curve is highlighted with a bold line. The smallest atrial contribution index is observed while the fourth A-V delay value is used. Hence, at step 312 of FIG. 5, the pacer/ICD sets the A-V delay to the first A-V delay value for use with subsequent DDI pacing, thereby optimizing the atrial contribution to pacing efficacy. Although not shown in FIG. 6, typically, a greater number of stroke volume curves are preferably obtained by iteratively adjusting the A-V delay through a greater number of values, thus allowing the pacer/ICD to select the optimal A-V delay from among a greater number of test A-V delay values. Note that, in this particular example, the largest atrial contribution index occurs at the A-V delay value that also provides the greatest overall stroke volume. In other cases, however, the largest atrial contribution index may occur at an A-V delay value that does not yield the largest stroke volume. In such cases, it is often preferred to set the A-V delay to the value that yields the largest overall stroke volume.

Figure 7:
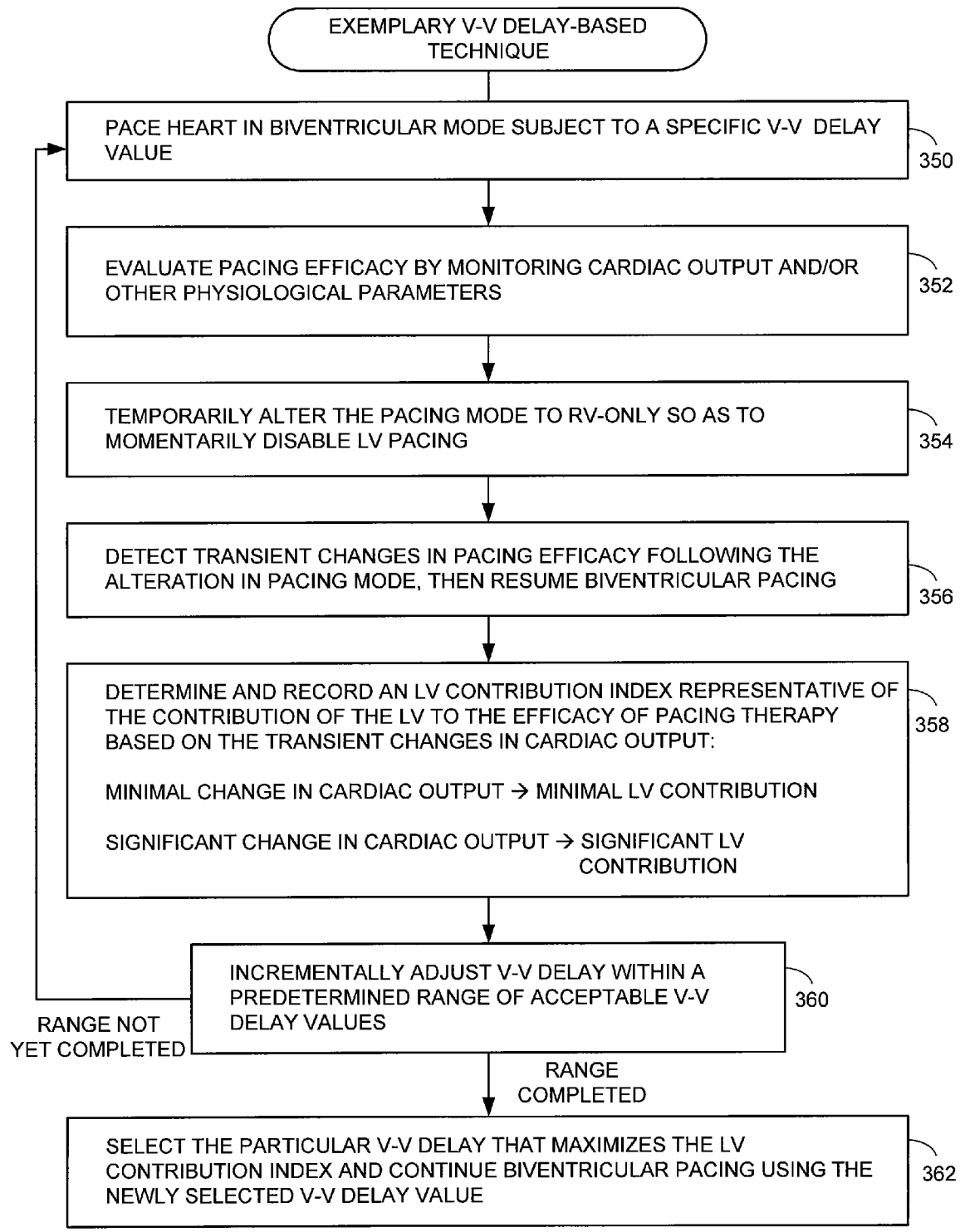
FIG. 7 is a flow chart illustrating a second exemplary implementation of the iterative technique of FIG. 4, wherein a V-V delay is iteratively adjusted to optimize the LV contribution to cardiac output during biventricular pacing.
Figure 8:
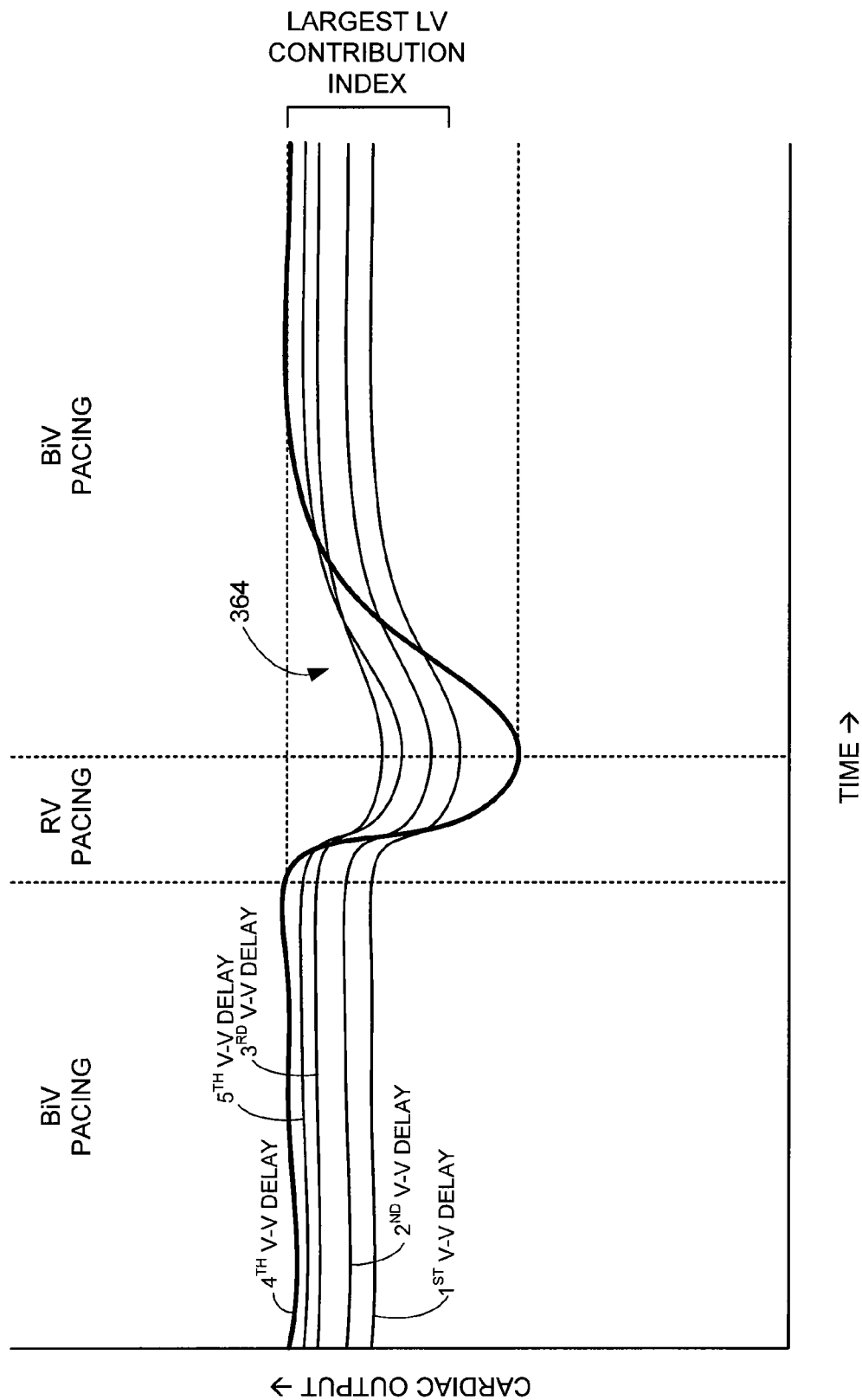
FIG. 8 is a graph illustrating a set of exemplary cardiac output curves and particularly illustrating transient reductions in cardiac output following temporary changes from biventricular to RV-only pacing performed in accordance with the technique of FIG. 7.

In the example of FIGS. 7-8, a V-V delay value is adjusted so as to optimize the LV contribution to cardiac performance, as measured by cardiac output. At step 350, the pacer/ICD paces the heart in a biventricular pacing mode wherein both the LV and RV are paced subject to a specific V-V delay value, which may be, e.g., a default value or a value set via a previous optimization session. At step 352, the pacer/ICD evaluates pacing efficacy by monitoring cardiac output and/or other relevant physiological parameters. At step 354, the pacer/ICD temporarily alters the pacing mode to RV-only (i.e. monoventricular) pacing so as to momentarily disable LV pacing. At step 356, the pacer/ICD detects transient changes in pacing efficacy following the switch to RV-only pacing, then resumes biventricular pacing. At step 358, the pacer/ICD determines and records an "LV contribution index" representative of the contribution of the LV to the efficacy of pacing therapy based on the transient changes in cardiac output. In this example, a minimal change in observed cardiac output is indicative of minimal contribution of the LV to pacing efficacy. A significant change in observed cardiac output is indicative of a more significant contribution of the LV to pacing efficacy. At step 360, the pacer/ICD incrementally adjusts the V-V delay within a predetermined range of acceptable V-V delay values, i.e. the pacer/ICD sets the V-V delay value to a different value within a predetermined range of acceptable V-V values already programmed into the device. Steps 350-358 are repeated at the new V-V delay value to assess the LV contribution to pacing efficacy at that new V-V delay value. Finally, once the range of values has been tested then, at step 362, the pacer/ICD selects the particular V-V delay that maximizes the LV contribution index and continues biventricular pacing using the newly selected V-V delay value so that the contribution of the LV to enhanced cardiac output is maximized.

FIG. 8 illustrates a set of five exemplary cardiac output curves 364 recorded during five iterations of the steps of FIG. 7. As with FIG. 6, the curves of FIG. 8 are shown superimposed over one another so as to emphasize the differences therebetween, although the curves are actually obtained sequentially over a period of time. A first curve illustrates the transient reduction in cardiac output observed while the V-V delay is set to a first specific V-V delay value (during biventricular pacing); a second curve illustrates the transient reduction in stroke volume observed while the V-V delay is set to a second specific V-V delay value (during biventricular pacing); and so on, up to a 5th V-V delay. In each case, the reduction in cardiac output from biventricular pacing to RV-only pacing is quantified as the LV contribution index, which represents the difference in cardiac output between the value observed just prior to the switch to RV-only pacing and the minimum value observed as a result of the switch to RV-only pacing. Hence, each curve has a different LV contribution index associate therewith. In this particular example, the largest LV contribution index is observed while the fourth V-V delay value is used. This particular curve is highlighted with a bold line. The smallest LV contribution index is observed while the first V-V delay value is used. Hence, at step 362 of FIG. 7, the pacer/ICD sets the V-V delay to the fourth V-V delay value for use with subsequent biventricular pacing, thereby optimizing the LV contribution to pacing efficacy. Although not shown in FIG. 8, typically, a greater number of cardiac output curves are preferably obtained by iteratively adjusting the V-V delay through a greater number of values, thus allowing the pacer/ICD to select the optimal V-V delay from among a greater number of tested V-V delay values.

What have been described are various exemplary techniques for evaluating and optimizing the contributions of particular heart chambers to pacing efficacy. The techniques have been described with respect to examples wherein the implantable system performs the evaluation and the optimization. However, principles of the invention are applicable to other systems. For example, the iterative adjustment in pacing parameters may instead be performed under the control of an external programmer. The transient changes in pacing efficacy can instead be detected using an external system. Exploitation of the invention within an implanted device is preferred as it allows the device itself to periodically evaluate the heart chamber contributions and adjust pacing parameters accordingly. For the sake of completeness, an exemplary pacer/ICD will now be described.

Exemplary Pacer/ICD

Figure 10:
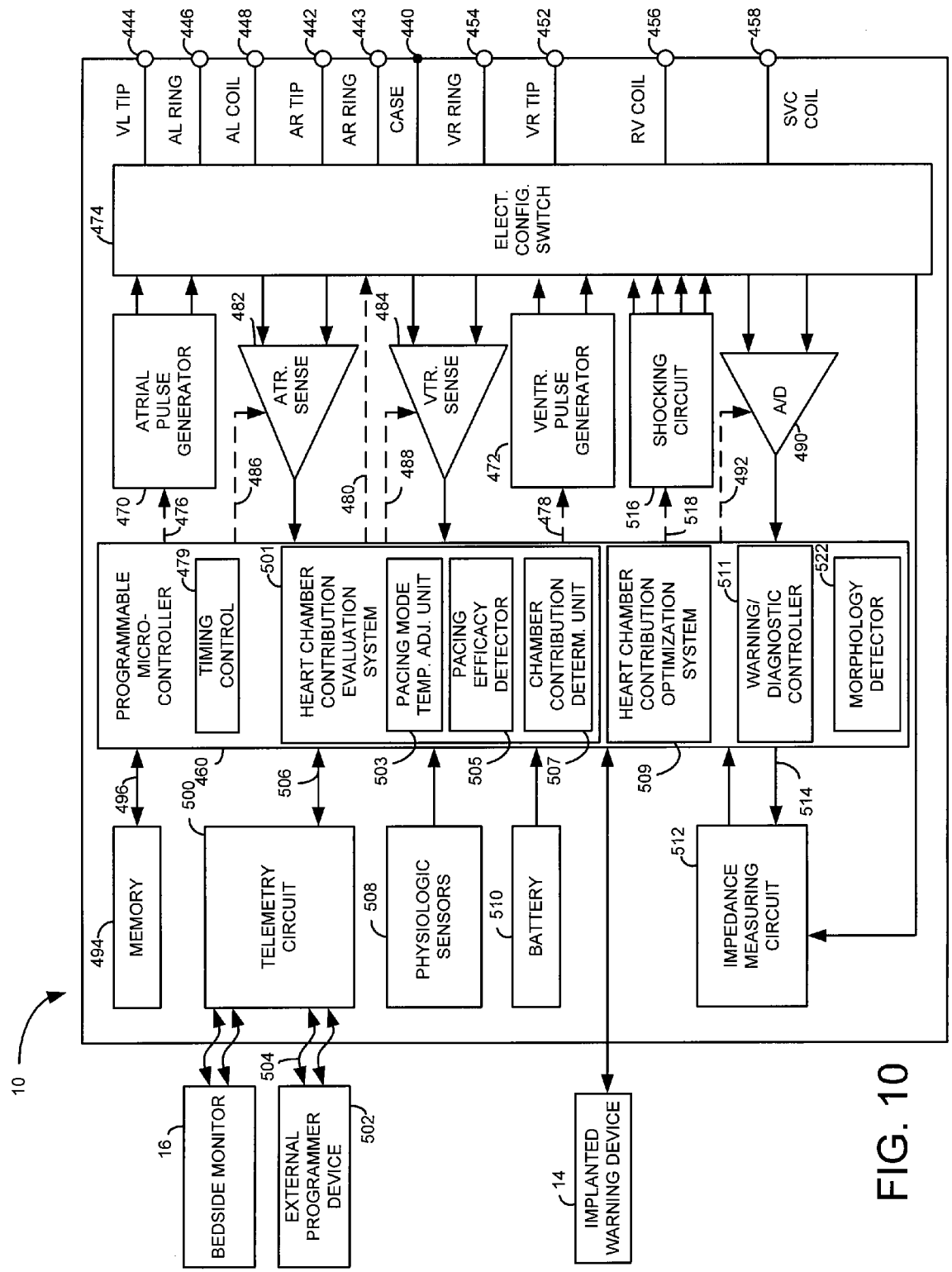
FIG. 10 is a functional block diagram of the pacer/ICD of FIG. 9, illustrating basic circuit elements that provide cardioversion, defibrillation and/or pacing stimulation in four chambers of the heart and particularly illustrating components for evaluating and optimizing heart chamber contributions to pacing efficacy.

With reference to FIGS. 9 and 10, an exemplary pacer/ICD will now be described. FIG. 9 provides a simplified block diagram of the pacer/ICD, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 10 is shown in electrical communication with a heart 412 by way of a left atrial lead 420 having an atrial tip electrode 422 and an atrial ring electrode 423 implanted in the atrial appendage. Pacer/ICD 10 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a CS lead 424 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 9, it should also be understood that additional stimulation leads (with one or more pacing, sensing and/or shocking electrodes) might be used in order to efficiently and effectively provide pacing stimulation to the left side of the heart or atrial cardioversion and/or defibrillation.

A simplified block diagram of selected internal components of pacer/ICD 10 is shown in FIG. 10. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 440 for pacer/ICD 10, shown schematically in FIG. 10, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($V_R$ COIL) 456, and an SVC shocking terminal (SVC COIL) 458, which are adapted for connection to the right ventricular tip electrode 432, right ventricular ring electrode 434, the $V_R$ coil electrode 436, and the SVC coil electrode 438, respectively. Although not shown, an additional terminal may be provided for coupling to an implantable warning device 14, if one is provided.

At the core of pacer/ICD 10 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 10, an atrial pulse generator 470 and a ventricular pulse generator 472 generate pacing stimulation pulses for delivery by the right atrial lead 420, the right ventricular lead 430, and/or the CS lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses. The microcontroller 460 further includes timing control circuitry (not separately shown) used to control the timing of such stimulation pulses (e.g., pacing rate, atrioventricular (A-V) delay, atrial interconduction (inter-atrial or A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, CS lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 10 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate ventricular tachycardia, high rate ventricular tachycardia, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the CS lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 494 through a telemetry circuit 500 in telemetric communication with the external device 502, such as a programmer, transtelephonic transceiver or a diagnostic system analyzer, or with a beside monitor 16. The telemetry circuit 500 is activated by the microcontroller by a control signal 506. The telemetry circuit 500 advantageously allows intracardiac electrograms and status information relating to the operation of pacer/ICD 10 (as contained in the microcontroller 460 or memory 494) to be sent to the external device 502 through an established communication link 504. Pacer/ICD 10 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, A-V delay, V-V delay, etc.) at which the atrial and ventricular pulse generators, 470 and 472, generate stimulation pulses. While shown as being included within pacer/ICD 10, it is to be understood that the physiologic sensor 508 may also be external to pacer/ICD 10, yet still be implanted within or carried by the patient.

A common type of rate responsive sensor is an activity sensor incorporating an accelerometer or a piezoelectric crystal, which is mounted within the housing 440 of pacer/ICD 10. Other types of physiologic sensors are also known, for example, sensors that sense the oxygen content of blood, respiration rate and/or minute ventilation, pH of blood, ventricular gradient, PPG etc. Multiple sensors may be provided.

The pacer/ICD additionally includes a battery 510, which provides operating power to all of the circuits shown in FIG. 10. The battery 510 may vary depending on the capabilities of pacer/ICD 10. If the system only provides low voltage therapy, a lithium iodine or lithium copper fluoride cell may be utilized. For pacer/ICD 10, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 10 is preferably capable of high voltage therapy and appropriate batteries.

As further shown in FIG. 10, pacer/ICD 10 is shown as having an impedance measuring circuit 512 which is enabled by the microcontroller 460 via a control signal 514. Thoracic impedance may be detected for use in tracking thoracic respiratory oscillations; lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with a VS event and/or pertaining to the treatment of tachycardia. Defibrillation shocks are generally of moderate to high energy level (i.e., corresponding to thresholds in the range of 5-40 joules), delivered asynchronously (since VS events may be too disorganized), and pertaining exclusively to the treatment of fibrillation. Accordingly, the microcontroller 460 is capable of controlling the synchronous or asynchronous delivery of the shocking pulses.

Insofar as heart chamber evaluation and optimization are concerned, the microcontroller includes a heart chamber contribution evaluation system 501 operative to evaluate the contribution of particular heart chambers to the overall efficacy of pacing therapy based on a temporary alteration in pacing mode and based on any transient changes in the efficacy of the pacing therapy following the alteration in pacing mode, in accordance with the techniques described above in connection with FIGS. 1-8. System 501 includes various components such as: a pacing mode temporary adjustment unit 503 operative to temporarily alter the pacing mode with which pacing therapy is delivered; a pacing efficacy detector 505 operative to detect transient changes in the efficacy of pacing therapy following the alteration in pacing mode; and a heart chamber contribution determination unit 507 operative to determine the contribution of the particular heart chambers to the overall efficacy of pacing therapy based on the alteration in pacing mode and based on the transient changes in the effectiveness of the pacing therapy. Additionally, the microcontroller includes a heart chamber optimization system 509 operative to adjust the pacing parameters based on the contribution of the particular heart chambers to the overall efficacy of pacing therapy. This may be achieved using the various optimization techniques described above with reference to FIGS. 4-8. A warning/diagnostics controller 511 controls the generation of warning signals and the storage of diagnostics data pertaining to the heart chamber evaluation and optimization procedures. Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use in delivering cardiac pacing therapy to the heart of a patient in which an implantable cardiac stimulation device is implanted, the method comprising the steps of:
   delivering cardiac pacing therapy to the heart of a patient using a pacing mode, the pacing mode specifying which chambers of the heart are paced;
   temporarily altering the pacing mode with which pacing therapy is delivered;
   detecting transient changes in the efficacy of pacing therapy following the alteration in pacing mode;
   determining the contribution of particular heart chambers to the overall efficacy of pacing therapy based on the alteration in the pacing mode and on any transient changes in the efficacy of the pacing therapy; and
   recording diagnostic information indicative of the contribution of particular heart chambers to the overall efficacy of pacing therapy.

2. The method of claim 1 further comprising adjusting selected pacing parameters so as to optimize the contribution of a particular heart chamber to the overall efficacy of pacing therapy.

3. The method of claim 2 wherein adjusting selected pacing parameters comprises:
   incrementally adjusting V-V delay values throughout a range of V-V values;
   temporarily switching the pacing mode from biventricular pacing to RV-only pacing at each particular V-V value; and
   determining the contribution of the LV to pacing efficacy at each particular V-V value.

4. The method of claim 3 wherein adjusting selected pacing parameters further comprising selecting the V-V value that yields the greatest contribution of the LV to pacing efficacy for use in further biventricular pacing.

5. The method of claim 2 wherein adjusting selected pacing parameters so as to optimize the contribution of the particular heart chamber to the overall efficacy of pacing therapy comprises:
   incrementally adjusting A-V delay values throughout a range of A-V values;
   temporarily switching from dual-chamber pacing to ventricular-only pacing at each particular A-V value; and
   evaluating the contribution of the atria to pacing efficacy at each particular A-V value.

6. The method of claim 5 wherein adjusting selected pacing parameters further comprising selecting the A-V value that yields the greatest contribution of the atria to pacing efficacy for use in further dual-chamber pacing.

7. The method of claim 1 wherein temporarily altering the pacing mode is performed by switching between a biventricular pacing mode and a monoventricular pacing mode.

8. The method of claim 1 wherein temporarily altering the pacing mode is performed by switching between a dual-chambered pacing mode, wherein pacing is performed in both the atria and ventricles, and a non-dual-chambered pacing mode, wherein pacing is exclusively performed in either the atria or the ventricles.

9. The method of claim 1 wherein temporarily altering the pacing mode is performed by switching among any of: AAI; VVI; DDD; DDI; VDD; and VOO pacing modes.

10. The method of claim 1 wherein temporarily altering the pacing mode is performed for a duration in the range of two to sixty seconds.

11. The method of claim 1 wherein detecting transient changes in the efficacy of pacing therapy following the alteration in pacing mode includes the steps of:
   sensing signals representative of the effectiveness of pacing therapy; and
   detecting any transient changes in the signals.

12. The method of claim 11 wherein sensing signals representative of the effectiveness of pacing therapy includes sensing signals representative of one or more of: morphological features of an intracardiac electrogram (IEGM); blood oxygen saturation; blood pressure; contractility; stroke volume; cardiac output; and a heart output pulse waveform.

13. The method of claim 11 wherein detecting transient changes in the signals includes detecting transient changes in the peak amplitude of the signals.

14. The method of claim 1 wherein determining the contribution of particular heart chambers to the overall efficacy of pacing therapy includes:
   detecting a lack of contribution by a particular heart chamber, if there is no significant change in the efficacy of pacing therapy following the alteration in the pacing mode; and
   detecting a significant contribution by a particular heart chamber, if there is significant change in the efficacy of pacing therapy following the alteration in pacing mode.

15. A method for use in delivering cardiac pacing therapy to the heart of a patient in which an implantable cardiac stimulation device is implanted, the method comprising the steps of:
   delivering cardiac pacing therapy to the heart of a patient using a pacing mode, the pacing mode specifying which chambers of the heart are paced;
   temporarily altering the pacing mode with which pacing therapy is delivered;
   detecting transient changes in the efficacy of pacing therapy following the alteration in pacing mode;
   determining the contribution of particular heart chambers to the overall efficacy of pacing therapy based on the alteration in the pacing mode and on any transient changes in the efficacy of the pacing therapy; and
   tracking changes over time in the contribution of particular heart chambers to the overall efficacy of pacing therapy.

16. The method of claim 15 further including the step of generating warning signals if the contribution of particular heart chambers to the overall efficacy of pacing therapy falls below a predetermined minimum acceptable amount.

17. The method of claim 15 wherein the heart is paced subject to one or more pacing parameters that affect the efficacy of pacing therapy and wherein the method further includes the step of adjusting the pacing parameters based on the contribution of particular heart chambers to the overall efficacy of pacing therapy.

18. The method of claim 17 wherein the pacing parameters include one or more of: an atrioventricular (A-V) delay; an inter-ventricular (V-V) delay; and an inter-atrial (A-A) delay.

19. The method of claim 17 wherein adjusting the pacing parameters is performed to increase the contribution of a particular heart chamber.

20. The method of claim 17 wherein adjusting the pacing parameters is performed to maximize the contribution of the particular heart chamber.

* * * * *

UNITED STATES PATENT AND TRADEMARK OFFICE
CERTIFICATE OF CORRECTION

PATENT NO. : 7,627,374 B1
APPLICATION NO. : 11/421936
DATED : December 1, 2009
INVENTOR(S) : Farazi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 636 days.

Signed and Sealed this

Second Day of November, 2010

David J. Kappos
*Director of the United States Patent and Trademark Office*